(12) United States Patent
Koch et al.

(10) Patent No.: US 7,847,014 B2
(45) Date of Patent: Dec. 7, 2010

(54) ADHESIVE EMULSION FOR MEDICAL PURPOSES MADE FROM ETHYLENE-VINYL ACETATE COPOLYMERS AND ADHESIVE RESINS

(75) Inventors: Andreas Koch, Melsbach (DE); Christoph Schmitz, Rheinbrohl (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 10/474,637

(22) PCT Filed: Mar. 30, 2002

(86) PCT No.: PCT/EP02/03584
§ 371 (c)(1),
(2), (4) Date: Dec. 9, 2003

(87) PCT Pub. No.: WO02/083107
PCT Pub. Date: Oct. 24, 2002

(65) Prior Publication Data
US 2004/0170673 A1 Sep. 2, 2004

(30) Foreign Application Priority Data
Apr. 12, 2001 (DE) .................. 101 18 282

(51) Int. Cl.
*C09J 131/04* (2006.01)
*C09J 193/04* (2006.01)
*B32B 7/12* (2006.01)
(52) U.S. Cl. ............... 524/563; 524/356; 524/270; 524/524; 428/343; 428/40.1; 428/41.7; 428/41.4; 424/443; 424/448; 424/449

(58) Field of Classification Search ............ 424/445, 424/448, 449
See application file for complete search history.

(56) References Cited

U.S. PATENT DOCUMENTS

| | | | | |
|---|---|---|---|---|
| 4,048,378 A | * | 9/1977 | Pelzek | 428/483 |
| 4,144,317 A | * | 3/1979 | Higuchi et al. | 424/435 |
| 4,194,995 A | * | 3/1980 | Schermann et al. | 524/42 |
| 4,814,168 A | | 3/1989 | Questel et al. | |
| 4,994,267 A | * | 2/1991 | Sablotsky | 514/182 |
| 5,662,923 A | | 9/1997 | Roreger | |
| 5,716,636 A | * | 2/1998 | Horstmann et al. | 424/448 |
| 5,942,583 A | * | 8/1999 | Azechi | 525/403 |

FOREIGN PATENT DOCUMENTS

| | | | |
|---|---|---|---|
| CA | 1333688 | * | 8/1988 |
| DE | 4230588 C1 | | 10/1993 |
| DE | 19501022 C1 | | 6/1996 |
| EP | 0 279 982 A | | 8/1988 |
| EP | 279982 A1 | * | 8/1988 |
| EP | 0 305 756 A | | 3/1989 |
| EP | 0 379 045 A1 | | 7/1990 |
| GB | 2 037 659 A | | 7/1980 |
| GB | 2037659 A | * | 7/1980 |

* cited by examiner

*Primary Examiner*—Callie E Shosho
*Assistant Examiner*—Anish Desai
(74) *Attorney, Agent, or Firm*—Birch, Stewart, Kolasch & Birch, LLP

(57) ABSTRACT

A pressure sensitive adhesive for medicinal application purposes, based on ethylene-vinyl acetate copolymers is characterized in that it contains as polymer component (A) an ethylene-vinyl acetate copolymer or a combination of at least two ethylene-vinyl acetate copolymers, and as component (B) an adhesive resin or a combination of adhesive resins at a portion of up to 55%-wt, relative to the sum of components (A) and (B) without active substances or other auxiliary substances.

9 Claims, 3 Drawing Sheets

ADHESIVE EMULSION FOR MEDICAL PURPOSES MADE FROM ETHYLENE-VINYL ACETATE COPOLYMERS AND ADHESIVE RESINS

This application is the national phase under 35 U.S.C. §371 of PCT International Application No. PCT/EP02/03584 which has an International filing date of Mar. 30, 2002, which designated the United States of America.

The present invention relates to pressure sensitive adhesives which are produced on the basis of ethylene-vinyl acetate copolymers and adhesive resins and which are suitable for medical application purposes, especially as a component of pressure-sensitive adhesive skin-contact layers. The invention further relates to pressure sensitive adhesive layers and active substance-containing pressure-sensitive adhesive matrix layers, as well as to transdermal therapeutic systems containing such pressure sensitive adhesives. The invention, in addition, comprises processes for the manufacture of such pressure sensitive adhesives, and of pressure sensitive adhesive layers and transdermal systems which use the pressure sensitive adhesives.

Pressure sensitive adhesives (PSA) are frequently utilized in the medical field for making self-adhesive skin-contact layers, for example in wound plasters or transdermal therapeutic systems (TTS). Such pressure sensitive adhesives can generally be regarded as high-viscous liquids which after shortly and slightly pressing them on the skin immediately and permanently adhere thereto. Due to their viscoelasticity, such pressure sensitive adhesive layers are very well capable of conforming to the skin surface of the various zones of the body. The pressure sensitive adhesives which are currently used most frequently are as a rule based on synthetic rubber polymers, polyacrylates or silicones.

In transdermal therapeutic systems, layers of pressure sensitive adhesive frequently simultaneously serve as an active substance reservoir. In this case, the pressure sensitive adhesive, apart from its function as adhesive, also has the function of an active substance reservoir and at the same time of controlling the release of active substance ("matrix-controlled TTS").

With regard to the reservoir function it must be borne in mind that the pressure sensitive adhesive used has to be compatible with the respective active substances which are being employed. In particular, the pressure sensitive adhesive must not lead to a degradation or decomposition of the active substance, and the chemical interactions between the pressure sensitive adhesive and the active substance should be as little as possible. In addition, it is demanded that the adhesive power of the active substance reservoir not be adversely affected even if larger amounts of active substance are incorporated.

Looking at the known compositions of the types of pressure sensitive adhesive of commercially available "matrix-controlled" TTS, pressure sensitive adhesives based on polyacrylates appear to best fulfil the above mentioned requirements. Apart from their very good autoadhesion, polyacrylates, by contrast to silicones and synthetic rubber polymers, have a high load capacity. Also of advantage is the relatively low skin irritating potential of polyacrylate-based pressure sensitive adhesive layers.

However, in polyacrylate pressure sensitive adhesives, the polarity or presence of functional groups in the polymer backbone can have disadvantageous effects; especially in the case of basic, but also of hydrolysis-unstable active substance compounds, there may occur stability and/or release problems as a result of chemical interactions. A further problem when using polyacrylates as pressure sensitive adhesive active substance matrix is the often necessary addition of chemical cross-linking agents in order to prevent "cold flow" (lateral flowing apart of the active substance matrix and emergence of the pressure sensitive adhesive mass at the lateral margins of the punched TTS during storage, due to insufficient cohesion in the pressure sensitive adhesive). However, the cross-linking agents added are frequently the cause of stability problems on account of chemical interactions with the active substances contained in the active substance reservoir of the TTS; if titanium-containing cross-linking agents are used, skin-irritations may occur, in addition.

In other types of TTS, copolymers of ethylene and vinyl acetate (EVA copolymers, e.g. the commercial product EVA-TANE®) are used as base material for the active substance reservoir, e.g. in the TTS "Nicoderm CQ" or in the TTS "Testoderm 15" for the active substances nicotine and testosterone, respectively. However, since EVA copolymers have no autoadhesion, i.e. they are not pressure sensitive adhesive, in certain TTS adhesion to the skin must be ensured by means of an additional pressure sensitive adhesive layer. In such TTS, EVA copolymers are moreover also used in the form of membranes serving as control membrane for controlling the active substance release ("membrane-controlled TTS"). In this type of TTS, the control of the drug delivery is accomplished by a drug-specific pore size (microporous control membrane) or by the membrane thickness or membrane composition, e.g. EVA control membrane. However, EVA control membranes, too, like EVA-based active substance reservoirs, possess no pressure sensitive adhesive properties.

The task underlying the invention was therefore to provide pressure-sensitive adhesive compositions that have good pressure sensitive adhesive properties, are as chemically inert as possible, especially with respect to medicinal active substances, and which have the above mentioned advantageous properties of the known polyacrylate pressure-sensitive adhesives. At the same time, it is demanded that to increase internal cohesion no addition of cross-linking agents should be necessary. Furthermore, the portion of polar or functional groups in the polymer backbone should at the same time be minimized. The pressure sensitive adhesive compositions are moreover to enable a control of the release of active substance.

Surprisingly, this task is solved by pressure sensitive adhesives based on ethylene-vinyl acetate (EVA) copolymers which according to claim 1 contain an addition of adhesive resin(s).

Consequently, a pressure sensitive adhesive according to the present invention contains a polymer component (A), which is an ethylene-vinyl acetate copolymer or a combination of at least two ethylene-vinyl acetate copolymers, and a component (B), which is an adhesive resin or a combination of adhesive resins, the portion of component B amounting to 55%-wt, relative to the sum of components (A) and (B) without active substances or other auxiliary substances (i.e. relative to the pure pressure sensitive adhesive).

The present invention is based on the surprising observation that novel pressure sensitive adhesives are obtained if EVA copolymers are dissolved using suitable organic solvents under addition of heat, and if then adhesive resins e added in a specific mixing ratio; it is not necessary here to add cross-linking agents or plasticizers.

In this connection, it is of advantage that the adhesive resin portion is relatively small, compared to pressure sensitive adhesives based on synthetic rubber polymers (e.g. styrene-isoprene-styrene (SIS) block copolymers or styrene-butadiene-styrene (SBS) block copolymers, which necessitate markedly over 60%-wt of adhesive resin additives to obtain sufficiently pressure-sensitive adhesive properties. Such a high content of adhesive resin can, however, lead to skin irritations.

By contrast, in the pressure sensitive adhesives according to the invention, an adhesive resin content of at the most 55%-wt (relative to the sum of components A and B, without active substances or other auxiliary substances) is needed in order to achieve the pressure-sensitive adhesive properties demanded. In this manner it is possible to maintain a low skin irritation potential.

Especially preferred is an adhesive resin portion in the range of from 45 to 55%-wt; adhesives with this composition have particularly good pressure sensitive adhesive properties. The adhesive resin portion (component B) should, however, be at least 25%-wt, still better at least 30%-wt.

Adhesive resin additives are known to those skilled in the art as hydrogenated colophonic acid derivatives. Hydrogenated colophonic acids or their derivatives have for quite some time been used as base materials in pressure sensitive adhesive patches. Colophonic acids are contained in the natural product colophony, which is obtained by distillation of softwood balsam or by extraction from softwood stubs of predominantly subtropic-Mediterranean climatic zones.

For producing the pressure sensitive adhesives according to the invention, such colophonic acids are preferably used as have been partially or completely hydrogenated, in order to protect them against the influence of oxygen and to increase their chemical inertia, and have been esterified at their carboxyl group to improve alkali stability and likewise to increase chemical inertia. Especially preferred in this connection are methyl esters, glycerol esters, pentaerythritol esters, maleic acid-modified pentaerythritol esters, maleic acid-modified glycerol esters, or triethylene glycol esters of hydrogenated colophonic acids. Apart from these, other skin-tolerated derivatives of hydrogenated colophony may be used, as well as corresponding esters of non-hydrogenated colophonic acids or of non-hydrogenated colophony.

As component A are preferably taken into consideration such ethylene-vinyl acetate copolymers as have a high vinyl acetate content of at least 28%-wt, relative to the monomer composition. Incorporation of the vinyl acetate monomer, which is more strongly polar compared to ethylene, leads to a reduction of the glass transition temperature and, in conjunction therewith, to a reduction of the crystalline portions in the EVA copolymers. As a consequence, viscosity is lowered, swellability increases, and the above-mentioned EVA copolymers—either with the above-described adhesive resins in suitable solvent mixtures, or from the melt—can form adhesive and readily processable (that is, liquid or spreadable) pressure sensitive adhesive masses.

Best results are obtained where the portion of the EVA copolymer(s) is in the range of from 46 to 55%-wt, relative to the sum of the components (A) and (B). Preferably, the portion of component (A) is at least 25%-wt, especially at least 15%-wt.

The pressure sensitive adhesive masses of the invention are, as described, produced on the basis of EVA copolymers and adhesive resins, which constitute the base components of these pressure sensitive adhesives. To make pressure sensitive adhesive layers or active substance-containing layers, it is possible to add active substances as well as additives such as e.g. skin penetration-enhancing substances. Preferably, the pressure-sensitive adhesive portion in an active substance-containing layer or active substance matrix amounts to at least 60%-wt, with particular preference at least 75%-wt.

By contrast, with the pressure sensitive adhesives according to the present invention, an addition of plasticizers or cross-linking agents for adjusting the adhesion or cohesion balance is not necessary; thus, according to one preferred embodiment such additives are not utilized. Preferably, there are also no other pressure sensitive adhesive polymers, such as polyacrylates, added to the pressure sensitive adhesives of the invention.

The pressure sensitive adhesives according to the present invention can be used in numerous ways for the production of active substance-free or active substance-containing layers with pressure-sensitive adhesion to the skin. They are, in particular, suitable for producing active substance-containing pressure sensitive adhesive layers or adhesive matrices for active substance release in the field of human or veterinary medicine, e.g. as components of transdermal therapeutic systems. Apart from this, these pressure sensitive adhesives can also be used in the manufacture of adhesive dressings, fixation patches or self-adhesive electrodes, or for the production of pressure sensitive adhesive layers of TTS which are per se not adhesive.

Because of their advantageous properties and their sufficient adhesion (FIG. 4) the pressure sensitive adhesives according to the invention are especially suited for the production of the active substance matrix of transdermal therapeutic systems.

Preferably, such a system is configured as a single-layer matrix system which consists of a substantially active substance-impermeable backing layer, and the actual active active-substance-containing matrix layer, as well as a detachable protective layer. A TTS matrix system designed in this way stands out for its relatively simple and economical manufacture. It is further preferred that the active substance matrix be a single-phase system.

Preferably the TTS according to the invention contain an active substance portion in the range of 0.1 to 50%-wt., relative to the pressure sensitive adhesive layer or the active substance matrix. According to a further preferred embodiment, the adhesive resin portion in the TTS amounts to less than 50%-wt, with particular preference 39 to 49%-wt, relative to the pressure sensitive adhesive layer or active substance matrix.

By the inventive combination of EVA copolymers with adhesive resin(s) to form a homogenous, single-phase pressure sensitive adhesive matrix, it is possible to combine the advantages of matrix-controlled and membrane-controlled reservoir systems in one system. This represents an essential advantage over the state of the art since the control membrane (due to lacking adhesive power) in membrane-controlled systems must usually be equipped with an additional, pressure sensitive adhesive layer or with a pressure sensitive adhesive margin (superimposed patch), which makes their manufacture more complicated.

In this connection it is of particular advantage that by selecting different portions of vinyl acetate or ethylene in the EVA copolymer (component A) it is possible to control the diffusion, respectively the release, of active substance (cf. FIGS. 1A,B and FIGS. 2A,B).

Because of this property of the pressure sensitive adhesives according to the invention, it is also possible to use these adhesives to produce control membranes which, by contrast to known control membranes, are pressure sensitive adhesive. Such pressure sensitive adhesive EVA control membranes or control layers can be used as control membrane in membrane-controlled reservoir systems or as additional skin spread (skin-contact layer) in matrix-controlled TTS if the matrix itself does not have adhesive properties.

The pressure sensitive adhesives according to the present invention can therefore be utilized for producing active substance-containing or active substance-free layers of TTS, as well as of control membranes or control layers. The invention thus relates to TTS having a structure that is known per se, comprising an active substance-containing matrix or an active substance reservoir, a backing layer and a detachable backing layer, these TTS containing at least one active substance-containing or active substance-free layer which is made from a pressure sensitive adhesive according to the invention or which contains such pressure sensitive adhesive.

The structure of the TTS according to the invention comprises—apart from an active substance matrix—an active substance-impermeable backing layer, and a likewise active substance-impermeable, peelable protective film.

Suitable as backing layer are first of all polyesters which are characterized by particular strength, but also other skin-tolerated plastics such as, for example, polyvinyl chloride, ethylene vinyl acetate, vinyl acetate, polyethylene, polypropylene, cellulose derivates and many others. In the individual case, the backing layer may be provided with an additional layer, e.g. by vapour deposition with metals or other diffusion-blocking additives such as silicon dioxide, aluminium oxide or similar substances known to those skilled in the art.

For the detachable protective layer, the same materials may be used as are used for the backing layer, provided that the film is made detachable by a suitable surface treatment such as, for example, siliconization. Other detachable protective layers may, however, also be used, such as polytetrafluoroethylene-treated paper, cellophane, polyvinyl chloride, or similar materials.

Apart from the active substance(s), the pressure sensitive adhesive matrix according to the present invention may optionally contain penetration-enhancing substances in principle known to those skilled in the art. Penetration enhancers compatible with the pressure sensitive adhesive matrix of the invention, and therefore preferred, are, for example, saturated or unsaturated fatty acids, straight-chain or branched fatty alcohols as well as their esters, polyhydric aliphatic alcohols, polyethylene glycols, sorbitane fatty acid esters as well as their derivatives or fatty alcohol ethoxylates obtainable by ethoxylation, or monocyclic monoterpenes. Penetration-enhancing substances are preferably added in a concentration of 0.1 to 30%-wt, relative to the pressure sensitive adhesives layer of the active substance matrix.

It has been found that the pressure sensitive adhesive layers on the basis of EVA copolymers and adhesive resins according to the invention are particularly suitable for transdermal delivery of hormones, especially of steroid hormones such as sex steroids, especially for natural and/or synthetic estrogens and gestagens, both singly as well as in combination, e.g. estrogen/gestagen combinations. In this connection it is of particular advantage that the systems according to the present invention show no tendency whatsoever towards recrystallization of the active substance contained therein. The active substance matrix may contain one or more estrogens, or estrogen(s) in combination with at least one gestagen. The total concentration of these hormones in this case amounts to 0.1 to 15%-wt, relative to the active substance matrix. In the case of an estrogen-gestagen combination, it has proved particularly advantageous if estrogen(s) and gestagen(s) are present in a molar ratio of 1:1 to 1:10.

Due to the mentioned properties of the pressure sensitive adhesives according to the present invention, these adhesives are not only suitable as a matrix for neutral medicinal active substances (FIGS. 1A,B and FIGS. 2A,B) but especially for the manufacture of active substance-containing layers containing active substance(s) which is/are subject to hydrolysis. Among these are, in particular, active substance molecules with acetyl function, preferably acetyl-salicylic acid or diamorphine, and acid or basic, or organic, ionic (FIG. 3) medicinal active substances or their pharmaceutically acceptable salts.

Because of the chemical inertia (due to the lack of polar or functional groups) of the pressure sensitive adhesives according to the invention towards medicinal active substances, chemical interactions with the active substances, such as irreversible acid-base reactions, are largely excluded. As a consequence, the release of active substance, and thereby bioavailability, can not be adversely affected by these unwanted reactions, which is not the case with pressure sensitive adhesive matrices based on acrylate adhesives.

Furthermore, the pressure sensitive adhesives according to the invention have a good reservoir capacity since most of the active substances, both lipophile and hydrophile, readily dissolve in EVA copolymers. It is, for example, possible to achieve active substance loads of 10%-wt. (relative to the active substance matrix) without the aid of solubilizers, e.g. with the highly hydrophile organic morphinium salt morphinium-N-acetyl glycinate (Example 3), or with the highly lipophile gestagen norethisterone acetate. Such high load capacities cannot be achieved with the pressure-sensitive adhesives based on polyisobutylene, or with silicone adhesives (load capacity maximally 5%-wt.); the latter are, in addition, very expensive.

The pressure sensitive adhesives and pressure sensitive adhesive layers according to the invention can be prepared both from the solution, using organic solvents or solvent mixtures, and from the melt. In solidified state, the inventive pressure sensitive adhesives prepared from the melt also possess the typical properties of pressure sensitive adhesives, i.e. strong adhesion, and good quick stick. These inventive pressure sensitive adhesives prepared from the melt are to be distinguished from hot melt adhesives, which are used for industrial purposes. With these hot melt adhesives, adhesion occurs during the cooling process, after the molten adhesive has been applied to the substrate. Because of the high melting temperature required for this process and the lack of quick stick, this type of hot melt adhesives, which are not pressure sensitive adhesives, is not suitable for the production of TTS or medicinal plasters.

To prepare the pressure sensitive adhesives according to the invention from the melt, first, esters of colophony are homogenized under elevated temperature (45-150° C., preferably 50-120° C., especially preferred ca. 100° C.) by kneading and melting. Subsequently, ethylene-vinyl acetate copolymer(s), and optionally active substance(s) and/or penetration enhancers, are added and worked into the molten adhesive mass, this is followed by homogenization. The active substance-containing or active substance-free adhesive mass thus obtained can now be applied to a detachable protective layer by means of a hot melt coating line (nozzle application system and/or extruder). The production can also be accomplished by extrusion.

To prepare the pressure sensitive adhesives according to the invention from a solution, ethylene-vinyl acetate copolymer(s) (component A) is/are dissolved at elevated temperature (preferably 40-75° C., especially 45-55° C.) in an organic solvent mixture, while stirring. Preferably, a gasoline- and/or propyl acetate-containing solvent mixture is used for this purpose, the following mixtures being particularly preferred: gasoline/propyl acetate (2:1), gasoline/butanone (1:1), gasoline/propyl acetate/butanone (1:1:1), hexane/propyl acetate/acetone (1:1:1) (all values refer to volume content). Subsequently adhesive resin(s) (component B) are incorporated by stirring and under homogenisation until complete dissolution occurs, likewise at elevated temperature as indicated. Addition of optional components (e.g. active substances, enhancers) and coating is performed as described above. To remove the solvents, the layer thus obtained is subjected to drying at elevated temperature (preferably at ca. 30-80° C., especially at 50° C.

In the following, the invention will be explained in more detail by way of examples and illustrations.

Using the prepared active substance-containing pressure sensitive adhesive matrix systems according to the invention, permeation measurements were performed on the in-vitro skin model by using human skin epidermis (FIG. 1-3), or with the aid of modified Franz diffusion cells. In all cases, the acceptor medium was isotonic saline with 0.1% addition of NaN3 as preserving agent, thermostatted to 37° C.

EXAMPLE 1

Preparing a Self-Adhesive, Active Substance-Containing Film (17-β-estradiol and Norethisterone Acetate)

In 80 g of a solvent mixture, consisting of 2 parts special boiling point gasoline type 80/110 and 1 part propyl acetate, is introduced 54 g of an EVA copolymer, with 40%-wt of vinyl acetate and a melt flow index of 55 (EVATANE 40/55®), and dissolved by stirring und under addition of heat at 50° C. After approx. 30 minutes of stirring, a viscous, colourless up to slightly opaque solution is obtained. In this solution was then introduced 66 g of the adhesive resin Foral® 85 E, and this was stirred, likewise at 50° C., until complete dissolution occurred (ca. 15 min). A 50%, low-viscous, yellowish and slightly opaque solution (adhesive solution I) resulted which after having cooled down was still present as a stirrable adhesive solution. To prepare the self-adhesive, active substance-containing film 9.88 g of adhesive solution I was used, into which 2.4 g of 17-β-estradiol, and subsequently 9.6 g of norethisterone acetate, were introduced in portions by stirring. If necessary, 1000 µl of methanol can be added to reduce the viscosity of the mass composition. This mass composition is homogenized for a total of 30 min at a stirring speed of 350 rpm. This is followed by degassing for 15 minutes at 45° C. in the ultrasonic bath to remove excessive air from the mass.

The active substance-containing adhesive solution is then, by means of a sheeting-out doctor knife, spread with a wet-layer thickness of 300 µm to a siliconised polyethylene terephthalate film. Thereafter the solvents are removed by drying for half an hour at 50° C. in a drying cupboard with waste air guidance. The solvent-free, active substance-containing adhesive film is subsequently covered with a 15-µm-thick polyester film (as backing layer) by laminating. The portion of adhesive contained in the matrix after completion of the preparation amounts to 88%-wt; of this, 48.4%-wt is made up by the adhesive resin.

EXAMPLE 2

Preparation of a Self-adhesive, Active Substance-Containing Film (17-β-estradiol and Norethisterone Acetate)

In 60 g of a solvent mixture, consisting of 2 parts special boiling-point gasoline type 80/110 and 1 part propyl acetate, is introduced 69 g of an EVA copolymer with 33%-wt of vinyl acetate and a melt index of 400 (EVATANE 33/400®) and dissolved by stirring and under addition of heat at 50° C. After stirring for ca. 30 min, a viscous, colourless up to slightly opaque solution was obtained. In this solution was then introduced 56 g of the adhesive resin Foral® 85 E and this was stirred, likewise at 50° C., until complete dissolution occurred (ca. 15 min). There resulted a 58%, low-viscous, yellowish and slightly opaque solution (adhesive solution II) which even after having cooled down was still present as a stirrable adheesive solution.

To prepare the self-adhesive, active substance-containing film, 7.59 g of adhesive solution II was used, into which 2.4 g of 17-β-estradiol and, subsequently, 9.6 g of norethisterone acetate were introduced in portions by stirring. The further preparation of the adhesive film was performed as described in Example 1.

The portion of adhesive in the matrix after completion of the preparation amounted to 88%-wt; of this, 39.6%-wt was made up by the portion of adhesive resin.

EXAMPLE 3

Preparation of a Self-Adhesive, Active Substance-Containing Film (morphinium-N-acetylglycinate as Active Substance)

The preparation is performed as described under Example 1, but with an adhesive resin portion of 49.5%-wt in the matrix, and with morphinium-N-acetylglycinate (10%-wt.) as active substance. EVATANE 40/55® was again used as EVA copolymer.

TABLE 1

Active substance-containing films according to Examples 1 to 3

| | Example 1 | Example 2 | Example 3 |
|---|---|---|---|
| EVA copolymer type | 40/55 | 33/400 | 40/55 |
| Vinyl acetate content in the copolymer (Gew.-%) | 40 | 33 | 40 |
| EVA content in the matrix (in %-wt.) | 39.6 | 48.4 | 40.5 |
| Adhesive resin portion in the matrix (%-wt) | 48.4 | 39.6 | 49.5 |
| Vinyl acetate content in the matrix (%-wt) | 15.84 | 15.972 | 16.20 |
| Ethylene portion in the matrix (%-wt) | 23.76 | 32.428 | 24.3 |
| Active substances (%-wt) | Oes: 2.4 NeA: 9.6 | Oes: 2.4 NeA: 9.6 | Morphinium-N-acetylglycinate: 10 |

As a comparison example was used a commercial reference combination TTS (Evorel Conti®; Cilag, CH) containing 2.5%-wt of 17-β-estradiol (as semihydrate), 8.75%-wt of norethisterone acetate, 2%-wt of Myprogat 90 and 86.75%-wt of Duro-Tak 2287. Myprogat 90 is a water-absorbing agent, not an enhancer.

Figure 1A:
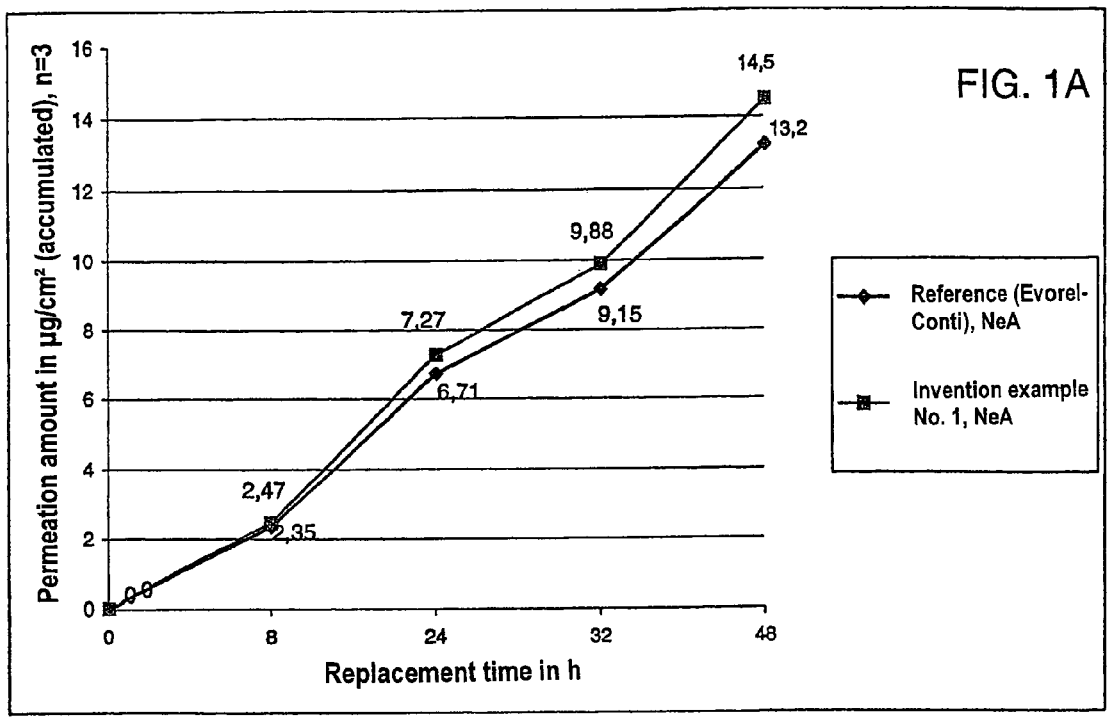
FIG. 1A shows results of permeation measurements with a recrystallisation-free matrix of the invention according to Example 1 with a portion of 48.4%-wt of adhesive resin, and 17-β-estradiol (2.4%-wt.; as semihydrate) and norethisterone acetate (9.6%-wt) as active substance, without addition of enhancers, cross-linking agents, plasticizers, crystallisation inhibitors or other auxiliaries.

FIG. 1A shows a comparison of the accumulated permeation values of norethisterone acetate (abbreviated: "NeA")

Figure 1B:
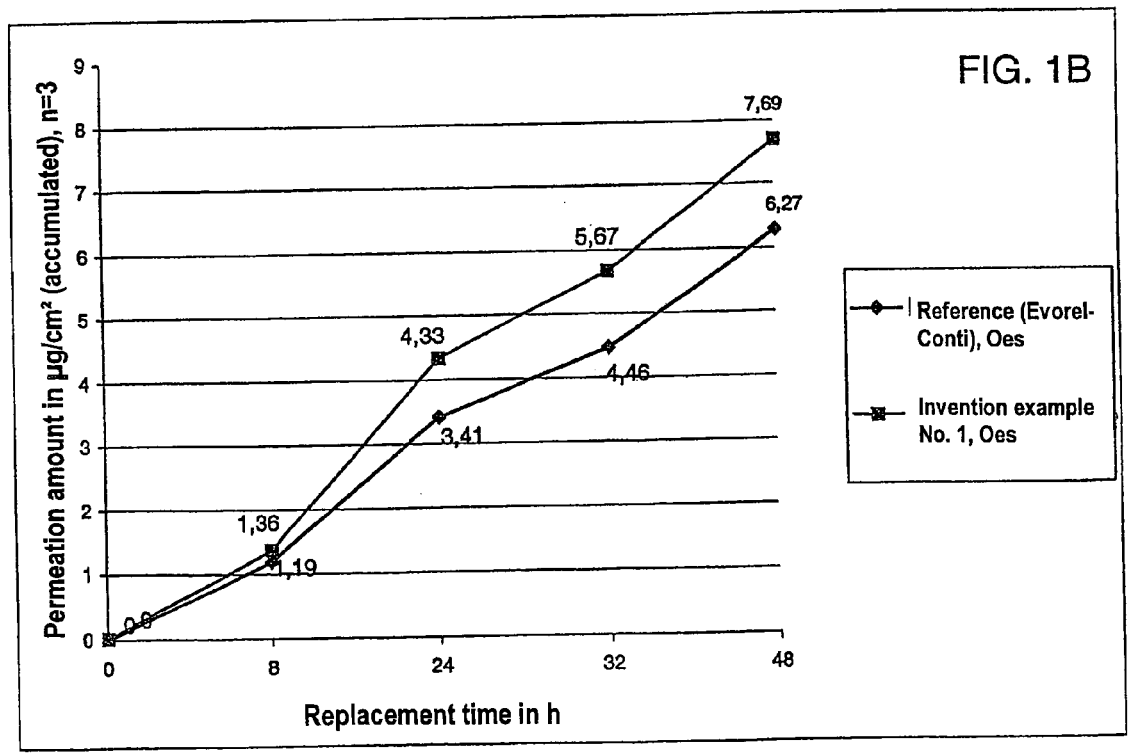
FIG. 1 to 3 show the results of the permeation measurements performed with Examples 1 to 3.

FIG. 1B:
Shows results of permeation measurements with a matrix of the invention according to Example 1, as in FIG. 1A, but here representing a comparison of the accumulated permeation values of 17-β-estradiol (abbreviated: "Oes").

Figure 2A:
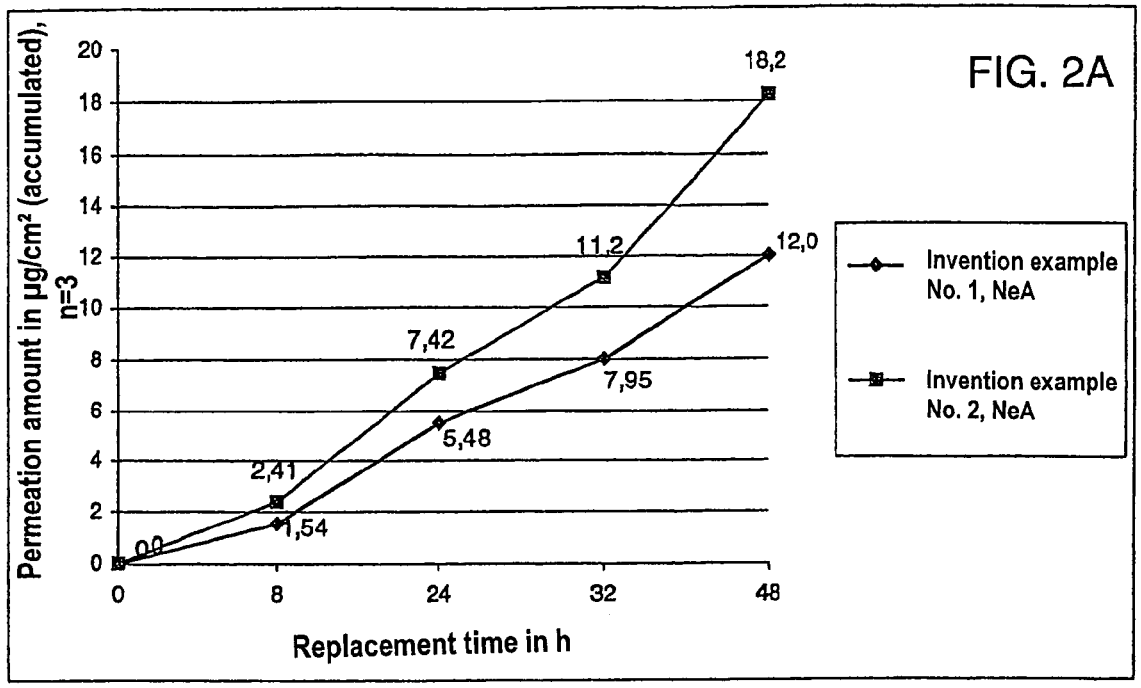

FIG. 2A:
Shows results of permeation measurements with a matrix of the invention according to Example 2 with a portion of 39.6%-wt of adhesive resin, a portion of 15.972%-wt of vinyl acetate (relative to the entire matrix), as well as 17-β-estradiol (2.4%-wt; as semihydrate) and norethisterone acetate (9.6%-wt) as active substances, without addition of enhancers, cross-linking agents, plasticizers, crystallisation inhibitors or other auxiliary substances. As comparison example was used a matrix of the invention according to Example 1 with almost the same portion of vinyl acetate (15.84%-wt), but lower ethylene content (23.76%-wt) and higher adhesive resin portion (48.4%-wt.).

FIG. 2A shows a comparison of accumulated permeation values of norethisterone acetate ("NeA").

Figure 2B:
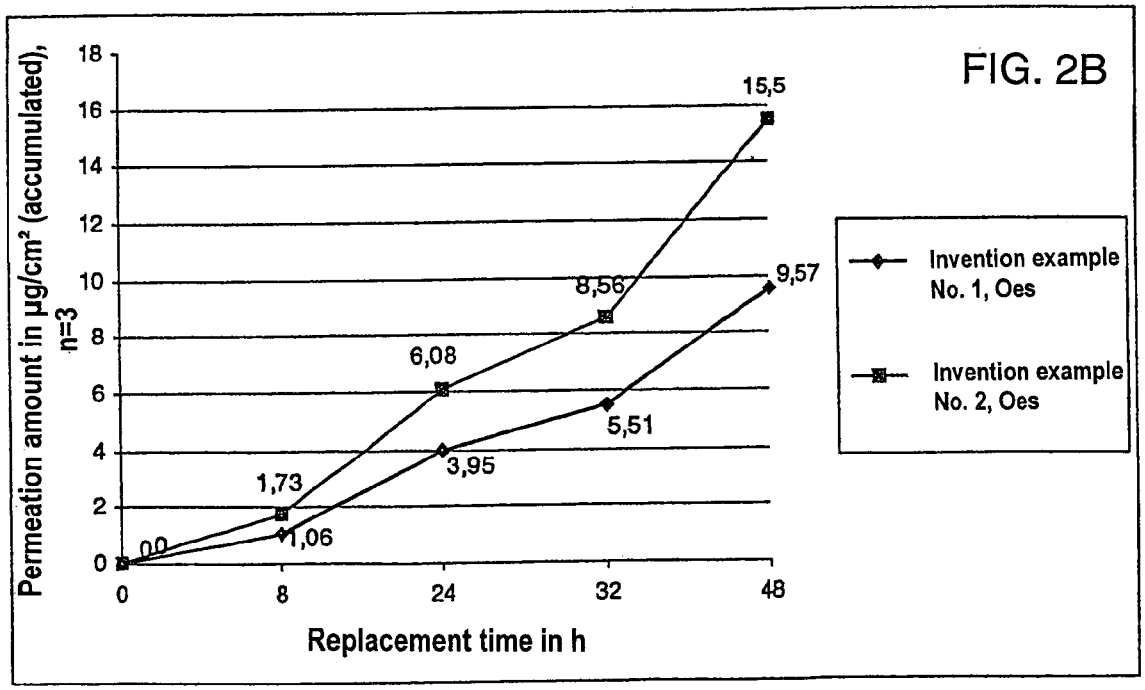

FIG. 2B:
shows results of permeation measurements with a matrix of the invention according to Example 2, as in FIG. 2A, but here representing a comparison of accumulated permeation values of 17-β-estradiol ("Oes").

Figure 3:
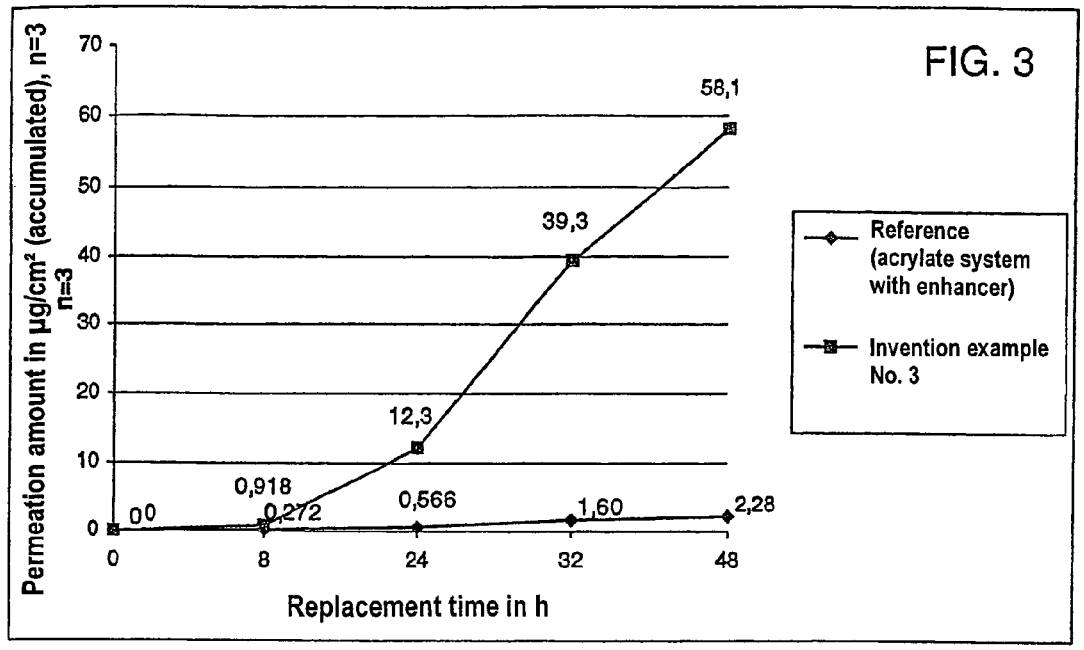

FIG. 3:
shows results of permeation measurements with a matrix of the invention according to Example 3 with a portion of 49.5%-wt of adhesive resin, and with morphinium-N-acetylglycinate as active substance, without addition of enhancers, cross-linking agents, plasticizers or other auxiliary substances.

As comparison example (reference) was used a pressure sensitive adhesive matrix based on polyacrylates with cross-linking agent and with 25%-wt of oleic acid as enhancer. The active substance load was the same in both cases (10%-wt).

Figure 4:
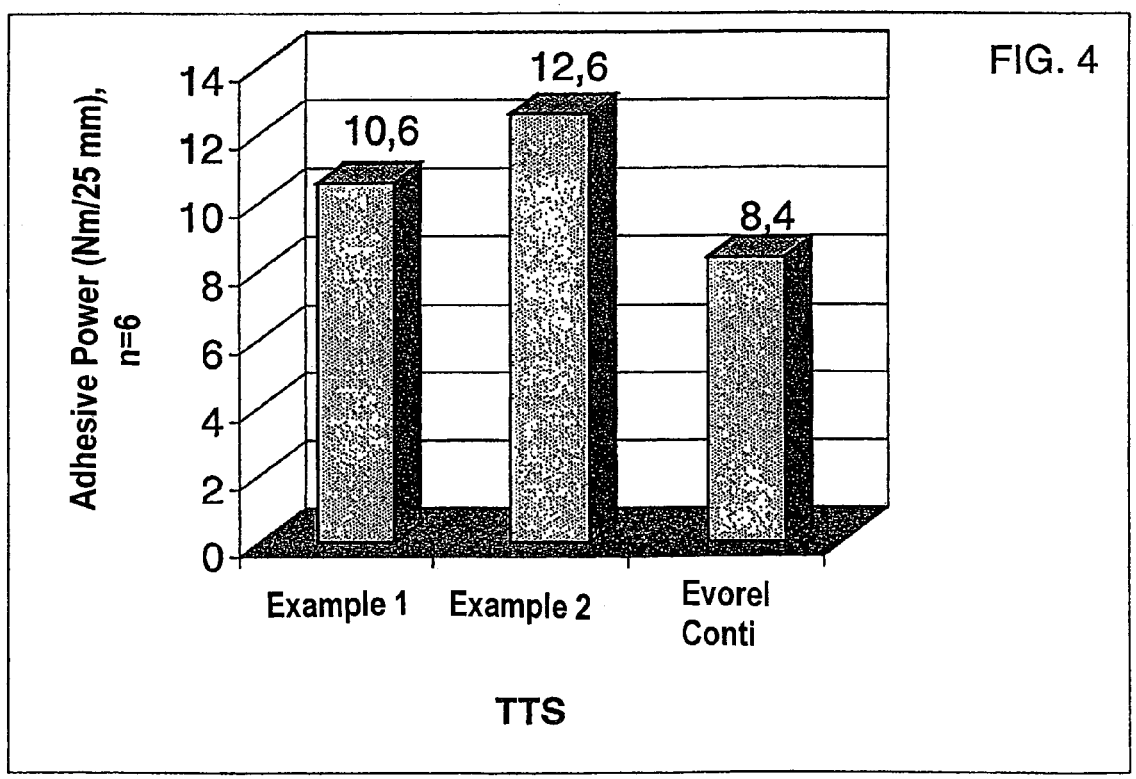

FIG. 4:
shows a comparison of values of adhesive power measured on TTS of the invention based on EVA copolymers and adhesive resins according to Examples 1 and 2, compared with adhesive power values of a reference TTS (Evorel Conti®) based on acrylate.

The measurements are based on the test method according to "Peel Adhesion 90° Test" (test plate: aluminium; peel-off speed 300 mm/min; tensile-testing machine according to DIN51221, part 1).

The invention claimed is:

1. A pressure sensitive adhesive composition based on ethylene-vinyl acetate copolymers, wherein the pressure sensitive adhesive composition consists of:
   (i) a polymer component (A), which is an ethylene-vinyl acetate copolymer or a combination of at least two ethylene-vinyl acetate copolymers, and
   (ii) a component (B), which is an adhesive resin or a combination of adhesive resins at a portion of up to 55%-wt, relative to the sum of the components (A) and (B),
   wherein components (A) and (B) are present in dissolved form in a mixture of organic solvents selected from the group consisting of gasoline/propyl acetate in proportion 2:1 by volume, gasoline/butanone in proportion 1:1 by volume, gasoline/propyl acetate/butanone in proportion 1:1:1 by volume and hexane/propyl acetate/acetone in proportion 1:1:1 by volume.

2. The pressure sensitive adhesive composition according to claim 1, wherein at least one of the ethylene-vinyl acetate copolymer(s) has a vinyl acetate content of at least 28%-wt, relative to the monomer composition.

3. The pressure sensitive adhesive composition according to claim 1, wherein said polymer component A is at least 46%-wt, relative to the sum of components A and B.

4. The pressure sensitive adhesive composition according to claim 1, wherein the portion of said component B is at least 45%-wt and up to 55%-wt, relative to the sum of components A and B.

5. The pressure sensitive adhesive composition according to claim 1, wherein the adhesive resin(s) are ester(s) of colophony and/or ester(s) of hydrogenated colophony.

6. The pressure sensitive adhesive composition according to claim 5, wherein the esters of colophony and/or esters of hydrogenated colophony are selected from the group consisting of methyl esters, glycerol esters, pentaerythritol esters, maleic-acid-modified pentaerythritol esters, maleic-acid-modified glycerol esters and triethylene glycol esters.

7. The pressure sensitive adhesive composition according to claim 1, wherein said pressure sensitive adhesive composition is free of any plasticizers and cross-linking agents.

8. A process for producing a pressure sensitive adhesive composition, comprising:
   i) dissolving at least one ethylene-vinyl acetate copolymer, as polymer component (A) in a mixture of organic solvents, at a temperature of from 40 to 75° C., wherein the mixture of organic solvents is selected from the group consisting of gasoline/propyl acetate in proportion 2:1 by volume, gasoline/butanone in proportion 1:1 by volume, gasoline/propyl acetate/butanone in proportion 1:1:1 by volume, and hexane/propyl acetate/acetone in proportion 1:1:1 by volume; and
   ii) incorporating an adhesive resin or a combination of adhesive resins as component B at a portion of up to 55%-wt relative to the sum of the components (A) and (B) into the mixture of step i) by stirring and homogenizing at a temperature of from 40 to 75° C. until complete dissolution occurs.

9. The process according to claim 8, wherein the adhesive resin is selected from the group consisting of esters of colophony and esters of hydrogenated colophony.

* * * * *